US008575405B2

(12) United States Patent
Lee et al.

(10) Patent No.: US 8,575,405 B2
(45) Date of Patent: *Nov. 5, 2013

(54) REDUCING ACETALS DURING ETHANOL SEPARATION PROCESS

(75) Inventors: David Lee, Seabrook, TX (US); Adam Orosco, Houston, TX (US); Lincoln Sarager, Houston, TX (US); R. Jay Warner, Houston, TX (US); Radmila Jevtic, Houston, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 161 days.

This patent is subject to a terminal disclaimer.

(21) Appl. No.: 13/197,737

(22) Filed: Aug. 3, 2011

(65) Prior Publication Data

US 2013/0035523 A1    Feb. 7, 2013

(51) Int. Cl.
 C07C 29/149    (2006.01)
(52) U.S. Cl.
 USPC ............................ 568/885; 568/913; 568/918
(58) Field of Classification Search
 USPC .......................................... 568/885, 913, 918
 See application file for complete search history.

(56) References Cited

U.S. PATENT DOCUMENTS

| | | | |
|---|---|---|---|
| 2,882,244 A | 4/1959 | Milton | |
| 3,102,150 A | 8/1963 | Hunter et al. | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,990,952 A | 11/1976 | Katzen et al. | |
| 4,275,228 A | 6/1981 | Gruffaz et al. | |
| 4,306,942 A | 12/1981 | Brush et al. | |
| 4,319,058 A | 3/1982 | Kulprathipanja et al. | |
| 4,372,822 A | 2/1983 | Muller et al. | |
| 4,379,028 A | 4/1983 | Berg et al. | |
| 4,398,039 A | 8/1983 | Pesa et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,569,726 A | 2/1986 | Berg et al. | |
| 4,626,321 A | 12/1986 | Grethlein et al. | |
| 4,678,543 A | 7/1987 | Houben et al. | |
| 4,692,218 A | 9/1987 | Houben et al. | |
| 4,842,693 A | 6/1989 | Wheldon | |
| 4,886,905 A | 12/1989 | Larkins et al. | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,124,004 A | 6/1992 | Grethlein et al. | |
| 5,144,068 A | 9/1992 | Smith et al. | |
| 5,149,680 A | 9/1992 | Kitson et al. | |
| 5,185,481 A | 2/1993 | Muto et al. | |
| 5,250,271 A | 10/1993 | Horizoe et al. | |
| 5,362,918 A | 11/1994 | Aizawa et al. | |
| 5,449,440 A | 9/1995 | Rescalli et al. | |
| 5,502,248 A | 3/1996 | Funk et al. | |
| 5,527,969 A | 6/1996 | Kaufhold et al. | |
| RE35,377 E | 11/1996 | Steinberg et al. | |
| 5,599,976 A | 2/1997 | Scates et al. | |
| 5,770,770 A | 6/1998 | Kim et al. | |
| 5,821,111 A | 10/1998 | Grady et al. | |
| 5,861,530 A | 1/1999 | Atkins et al. | |
| 5,973,193 A | 10/1999 | Crane et al. | |
| 5,993,610 A | 11/1999 | Berg | |
| 6,040,474 A | 3/2000 | Jobson et al. | |
| 6,093,845 A | 7/2000 | Van Acker et al. | |
| 6,143,930 A | 11/2000 | Singh et al. | |
| 6,232,352 B1 | 5/2001 | Vidalin et al. | |
| 6,375,807 B1 | 4/2002 | Nieuwoudt et al. | |
| 6,472,555 B2 | 10/2002 | Choudary et al. | |
| 6,509,180 B1 | 1/2003 | Verser et al. | |
| 6,627,770 B1 | 9/2003 | Cheung et al. | |
| 6,632,330 B1 | 10/2003 | Colley et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,723,886 B2 | 4/2004 | Allison et al. | |

(Continued)

FOREIGN PATENT DOCUMENTS

| | | |
|---|---|---|
| EP | 0104197 | 4/1984 |
| EP | 0167300 | 1/1986 |

(Continued)

OTHER PUBLICATIONS

International Search Report and Written Opinion mailed Dec. 7, 2012 in corresponding International Application No. PCT/US2011/046491.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

(Continued)

Primary Examiner — Elvis O Price

(57) ABSTRACT

To reduce acetal concentrations when separating ethanol from a crude product in one or more distillation column, at least one of the columns is operated at a higher pressure to increase the equilibrium constant that favors hydrolysis of the acetal. The crude product may comprise ethanol, acetaldehyde, water and one or more acetals, such as diethyl acetal. The acetal concentration may be reduced thus reducing the need to separate acetal from the crude product.

21 Claims, 6 Drawing Sheets

(56) References Cited

U.S. PATENT DOCUMENTS

| | | |
|---|---|---|
| 6,765,110 B2 | 7/2004 | Warner et al. |
| 6,768,021 B2 | 7/2004 | Horan et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,863,489 B2 | 1/2011 | Johnston et al. |
| 7,884,253 B2 | 2/2011 | Stites et al. |
| 7,888,082 B2 | 2/2011 | Verser et al. |
| 2003/0013908 A1 | 1/2003 | Horan et al. |
| 2006/0019360 A1 | 1/2006 | Verser et al. |
| 2006/0127999 A1 | 6/2006 | Verser et al. |
| 2007/0106246 A1 | 5/2007 | Modesitt |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0005588 A1 | 1/2009 | Hassan et al. |
| 2009/0023192 A1 | 1/2009 | Verser et al. |
| 2009/0069609 A1 | 3/2009 | Kharas et al. |
| 2009/0281354 A1 | 11/2009 | Mariansky et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |
| 2011/0028767 A1 | 2/2011 | Kikuchi et al. |

FOREIGN PATENT DOCUMENTS

| | | |
|---|---|---|
| EP | 0400904 | 5/1990 |
| EP | 0372847 | 6/1990 |
| EP | 0456647 | 11/1991 |
| EP | 2060553 | 5/2009 |
| EP | 2060555 | 5/2009 |
| EP | 2072487 | 6/2009 |
| GB | 2 053 915 A | 2/1981 |
| WO | WO 83/03409 | 10/1983 |
| WO | WO 2009/063176 | 5/2009 |
| WO | WO 2009/105860 | 9/2009 |
| WO | WO 2010/055285 | 5/2010 |

OTHER PUBLICATIONS

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

English abstract for EP0456647, 1991.

REDUCING ACETALS DURING ETHANOL SEPARATION PROCESS

FIELD OF THE INVENTION

The present invention relates generally to processes for producing ethanol and, in particular, to processes for separating ethanol from a crude product in one or more distillation columns that are operated at an increased pressure to reduce acetal concentration.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol mixture, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol product and a stream of acetic acid and ethyl acetate, which is recycled to the hydrogenation reactor.

U.S. Pat. No. 3,102,150 discloses hydrogenating aldehydes to alcohols using a hydrogenation catalyst and a cation exchange resin to reduce formation of acetals.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a method for producing ethanol comprising hydrogenating alkanoic acid and/or esters thereof in a reactor in the presence of a catalyst to form a crude ethanol mixture comprising acetaldehyde, ethanol, water, and diethyl acetal; and separating the crude ethanol mixture in the one or more columns to recover an ethanol product comprises less than 1 wt. % diethyl acetal, wherein at least one column is operated above atmospheric pressure. In one embodiment, the ethanol product may comprise from 0.0001 to 0.01 wt. % diethyl acetal.

In a second embodiment, the present invention is directed to a method for producing ethanol comprising hydrogenating alkanoic acid and/or esters thereof in a reactor in the presence of a catalyst to form a crude ethanol mixture, and separating a portion of the crude ethanol mixture in a first distillation column to yield a first residue comprising alkanoic acid, and a first distillate comprising ethanol, and acetaldehyde. A portion of the first distillate is further separated in a second distillation column operated above atmospheric pressure to yield a second residue comprising ethanol, and a second distillate comprising acetaldehyde. The second residues comprises less than 1 wt. % diethyl acetal.

In a third embodiment, the present invention is directed to a method for producing ethanol comprising providing a crude ethanol mixture comprising acetic acid, acetaldehyde, ethanol, water, and diethyl acetal; separating a portion of the crude ethanol mixture in a first distillation column to yield a first residue comprising acetic acid, and a first distillate comprising ethanol, and acetaldehyde; and separating a portion of the first distillate in a second distillation column operated above atmospheric pressure to yield a second residue comprising ethanol, and a second distillate comprising acetaldehyde, wherein the second residue comprises less than 1 wt. % diethyl acetal.

In a fourth embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column to yield a first residue comprising alkanoic acid, and a first distillate comprising ethanol, water, ethyl acetate, and acetaldehyde; separating a portion of the first distillate in a second distillation column operated above atmospheric pressure to yield a second residue comprising ethanol and water, and a second distillate comprising ethyl acetate and acetaldehyde; and separating a portion of the second residue in a third distillation column operated to yield a third residue comprising water, and a third distillate comprising ethanol, wherein the third distillate comprises less than 1 wt. % diethyl acetal.

In a fifth embodiment, the present invention is directed to a method for producing ethanol comprising providing a crude ethanol mixture comprising acetic acid, acetaldehyde, ethanol, water, and diethyl acetal; separating a portion of the crude ethanol mixture in a first distillation column to yield a first residue comprising acetic acid, and a first distillate comprising ethanol, water, ethyl acetate, and acetaldehyde; separating a portion of the first distillate in a second distillation column operated above atmospheric pressure to yield a second residue comprising ethanol and water, and a second distillate comprising ethyl acetate and acetaldehyde; and separating a portion of the second residue in a third distillation column operated to yield a third residue comprising water, and a third distillate comprising ethanol, wherein the third distillate comprises less than 1 wt. % diethyl acetal.

In another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in the first distillation column to yield a first residue comprising a substantial portion of the water fed to the distillation column, and a first distillate comprising ethanol, acetaldehyde, and water; removing water from the first distillate to yield an ethanol mixture stream; and separating a portion of the ethanol mixture stream in a second distillation column operated above atmospheric pressure to yield a second residue comprising ethanol, and a second distillate comprising acetaldehyde, wherein the second residue comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in the first distillation column to yield a first residue comprising a substantial portion of the water fed to the distillation column, and a first distillate comprising ethanol, ethyl acetate, acetaldehyde, and water; removing water from the first distillate to yield an ethanol mixture stream; separating a first portion of the ethanol mixture stream in a second distillation column operated above atmospheric pressure to yield a second residue comprising ethanol, and a second distillate comprising ethyl acetate and acetaldehyde, wherein the second residue comprises less than 1 wt. % diethyl acetal; separating a second portion of the ethanol mixture stream in a third distillation column operated a pressure from 0.1 to 100 kPa to yield a third residue comprising ethanol, and a third distillate comprising ethyl acetate and acetaldehyde, wherein the third residue comprises less than 1 wt. % ethyl acetate; and recovering an ethanol product from the second residue and/or third residue.

In yet another embodiment, the present invention is directed to a method for producing ethanol comprising hydrogenating alkanoic acid and/or esters thereof in a reactor in the presence of a catalyst to form a crude ethanol mixture comprising ethanol, water, ethyl acetate, acetaldehyde, and diethyl acetal; separating a portion of the crude ethanol mixture in the first distillation column to yield a first residue comprising a substantial portion of the water fed to the distillation column, and a first distillate comprising ethanol, ethyl acetate, acetaldehyde, and water; removing water from the first distillate to yield an ethanol mixture stream; separating a portion of the ethanol mixture stream in a second distillation column operated above atmospheric pressure to yield a second residue comprising ethanol, and a second distillate comprising ethanol, ethyl acetate and acetaldehyde, wherein the second residue comprises less than 1 wt. % diethyl acetal; separating a portion of the second distillate in a third distillation column operated a pressure from 0.1 to 100 kPa to yield a third residue comprising ethanol, and a third distillate comprising ethyl acetate and acetaldehyde, wherein the third residue comprises less than 1 wt. % ethyl acetate; and recovering an ethanol product from the second residue and/or third residue.

In yet another embodiment, the present invention is directed to a method for producing ethanol comprising hydrogenating alkanoic acid and/or esters thereof in a reactor in the presence of a catalyst to form a crude ethanol mixture comprising ethanol, water, ethyl acetate, acetaldehyde, and diethyl acetal; separating a portion of the crude ethanol mixture in the first distillation column to yield a first residue comprising a substantial portion of the water fed to the first distillation column, and a first distillate comprising ethanol, ethyl acetate, acetaldehyde, and water; removing water from the first distillate to yield an ethanol mixture stream; separating a portion of the ethanol mixture stream in a second distillation column operated a pressure from 0.1 to 100 kPa to yield a second residue comprising ethanol, and a second distillate comprising ethyl acetate and acetaldehyde, wherein the second residue comprises less than 1 wt. % ethyl acetate; separating a portion of the second distillate in a third distillation column operated above atmospheric pressure to yield a third distillate comprising acetaldehyde, and a third residue comprising ethanol, wherein the third residue comprises less than 1 wt. % diethyl acetal; and recovering an ethanol product from the second residue and/or third residue.

In yet another embodiment, the present invention is directed to a method for producing ethanol comprising providing a crude ethanol mixture comprising acetic acid, water, acetaldehyde, ethanol, and diethyl acetal; separating a portion of the crude ethanol mixture in the first distillation column to yield a first residue comprising a substantial portion of the water fed to the distillation column, and a first distillate comprising ethanol, acetaldehyde, and water; removing water from the first distillate to yield an ethanol mixture stream; and separating a portion of the ethanol mixture stream in a second distillation column operated above atmospheric pressure to yield a second residue comprising ethanol, and a second distillate comprising acetaldehyde, wherein the second residue comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column operated above atmospheric pressure to yield a first residue comprising alkanoic acid, and a first distillate comprising ethanol, and acetaldehyde; and separating a portion of the first distillate in a second distillation column to yield a second residue comprising ethanol, and a second distillate comprising acetaldehyde, wherein the second residue comprises less than 1 wt. % diethyl acetal.

In yet another embodiment, the present invention is directed to a method for producing ethanol comprising providing a crude ethanol mixture comprising acetic acid, acetaldehyde, ethanol, and diethyl acetal; separating a portion of the crude ethanol mixture in a first distillation column operated above atmospheric pressure to yield a first residue comprising acetic acid, and a first distillate comprising ethanol, and acetaldehyde; and separating a portion of the first distillate in a second distillation column to yield a second residue comprising ethanol, and a second distillate comprising acetaldehyde, wherein the second residue comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column operated above atmospheric pressure to yield a first residue comprising ethanol, and water, and a first distillate comprising ethyl acetate, and acetaldehyde; and separating a portion of the first residue in a second distillation column to yield a second residue comprising water, and a second distillate comprising ethanol, wherein the second distillate comprises less than 1 wt. % diethyl acetal.

In yet another embodiment, the present invention is directed to a method for producing ethanol comprising providing a crude ethanol mixture comprising acetic acid, acetaldehyde, ethyl acetate, ethanol, and diethyl acetal; separating a portion of the crude ethanol mixture in a first distillation column operated above atmospheric pressure to yield a first residue comprising acetic acid, ethanol, and water, and a first distillate comprising ethyl acetate, and acetaldehyde; and separating a portion of the first residue in a second distillation column to yield a second residue comprising water and acetic acid, and a second distillate comprising ethanol, wherein the second distillate comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture comprising alkanoic acid, water, acetaldehyde, ethanol, and diethyl acetal; and separating the crude ethanol mixture in the one or more columns to recover an ethanol product comprises less than 1 wt. % diethyl acetal, wherein at least one column has a stripping section that comprises at least 40 stages.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column to yield a first residue comprising alkanoic acid, and a first distillate comprising ethanol, and acetaldehyde; and separating a portion of the first distillate in a second distillation column having a stripping section that comprises at least 40 stages to yield a second residue comprising ethanol, and a second distillate comprising acetaldehyde, wherein the second residue comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column to yield a first residue comprising alkanoic acid, and a first distillate comprising ethanol, water, ethyl acetate, and acetaldehyde; separating a portion of the first distillate in a second distillation column having a stripping section that comprises at least 40 stages to yield a second residue comprising ethanol and water, and a second distillate comprising ethyl acetate and acetaldehyde; and separating a portion of the second residue in a third distillation column operated to yield a third residue comprising water, and a third distillate comprising ethanol, wherein the third distillate comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in the first distillation column to yield a first residue comprising a substantial portion of the water fed to the distillation column, and a first distillate comprising ethanol, acetaldehyde, and water; removing water from the first distillate to yield an ethanol mixture stream; and separating a portion of the ethanol mixture stream in a second distillation column having a stripping section that comprises at least 40 stages to yield a second residue comprising ethanol, and a second distillate comprising acetaldehyde, wherein the second residue comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column having a stripping section that comprises at least 40 stages to yield a first residue comprising ethanol, and water, and a first distillate comprising ethyl acetate, and acetaldehyde; and separating a portion of the first residue in a second distillation column to yield a second residue comprising water, and a second distillate comprising ethanol, wherein the second distillate comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column to yield a first residue comprising alkanoic acid, and a first distillate comprising ethanol, water, ethyl acetate, and acetaldehyde; separating a portion of the first distillate in a second distillation column having a stripping section that comprises at least 40 stages to yield a second residue comprising ethanol and water, and a second distillate comprising ethyl acetate and acetaldehyde; and separating a portion of the second residue in a third distillation column operated to yield a third residue comprising water, and a third distillate comprising ethanol, wherein the third distillate comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in the first distillation column to yield a first residue comprising a substantial portion of the water fed to the distillation column, and a first distillate comprising ethanol, acetaldehyde, and water; removing water from the first distillate to yield an ethanol mixture stream; and separating a portion of the ethanol mixture stream in a second distillation column having a stripping section that comprises at least 40 stages to yield a second residue comprising ethanol, and a second distillate comprising acetaldehyde, wherein the second residue comprises less than 1 wt. % diethyl acetal.

In yet another embodiment, the present invention is directed to a method for producing ethanol comprising hydrogenating alkanoic acid and/or esters thereof in a reactor in the presence of a catalyst to form a crude ethanol mixture; separating a portion of the crude ethanol mixture in a first distillation column having a stripping section that comprises at least 40 stages to yield a first residue comprising ethanol, and water, and a first distillate comprising ethyl acetate, and acetaldehyde; and separating a portion of the first residue in a second distillation column to yield a second residue comprising water, and a second distillate comprising ethanol, wherein the second distillate comprises less than 1 wt. % diethyl acetal.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
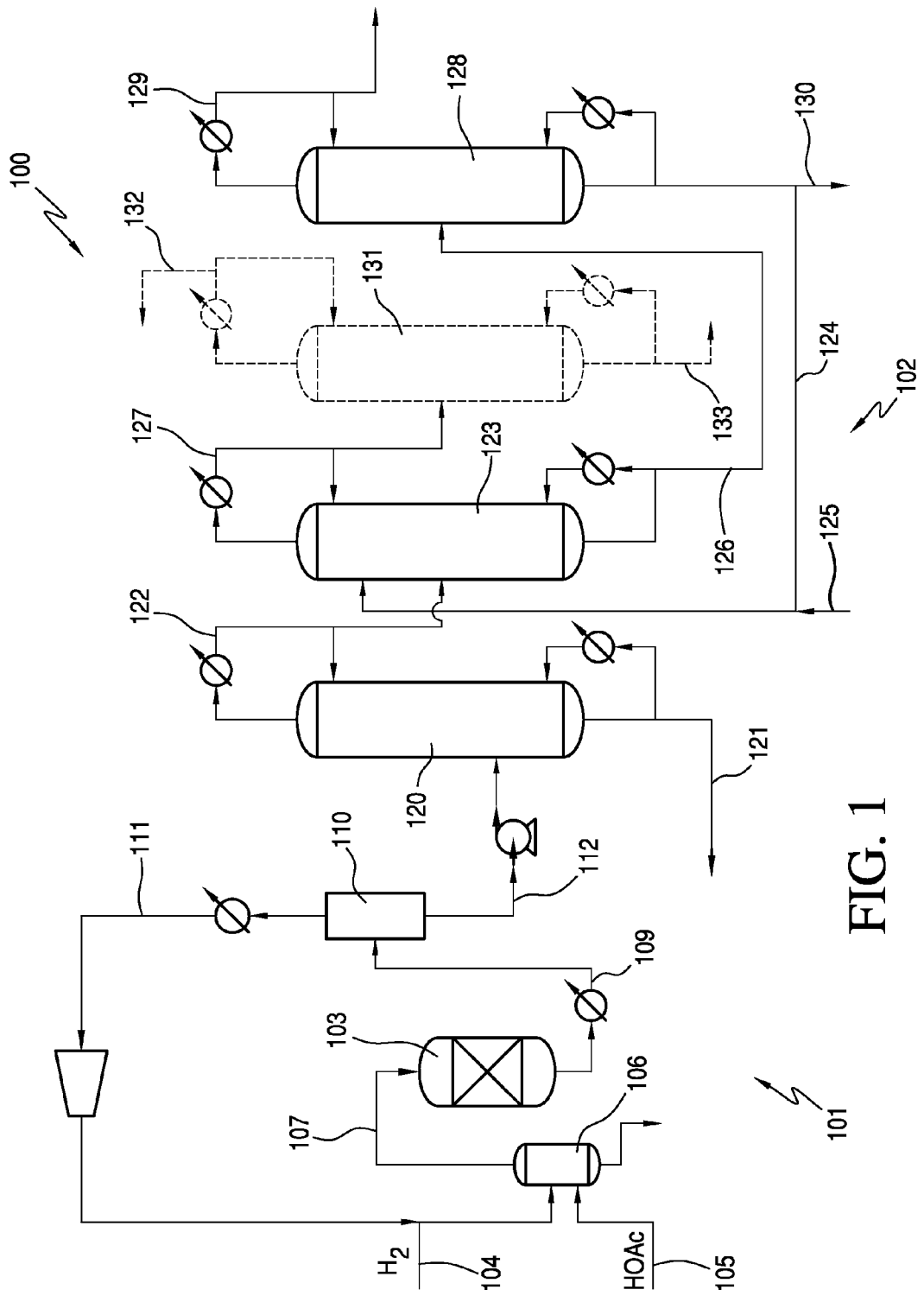
FIG. 1 is a schematic diagram of a hydrogenation process having four columns in accordance with an embodiment of the present invention.

The present invention relates to processes for recovering the ethanol from a crude mixture obtained by hydrogenating alkanoic acids and/or esters thereof. During hydrogenation several other organics may be formed along with ethanol in the crude mixture. The organics may also be formed during ethanol recovery and thus further reduce yields of ethanol. In particular, aldehydes may be present in the crude mixture and acetalization of the aldehyde may produce acetals. When acetic acid is hydrogenated to ethanol, acetaldehyde may be formed as an intermediate. The acetalization of acetaldehyde (AcH) to diethyl acetal (DEA) is an equilibrium reaction as shown:

$$Keq = \frac{[AcH][EtOH]}{[DEA][H_2O]}$$

Due to the relatively large ethanol concentration compared to acetaldehyde and/or diethyl acetal concentrations in the crude mixture, the equilibrium may favor acetalization. Further, the reaction mixture may contain acetic acid, and the acetalization reaction may be further catalyzed in the presence of mineral acids or carboxylic acids. Thus, diethyl acetal concentrations may increase during the recovery of ethanol from the crude mixture. Diethyl acetal may be difficult to remove from ethanol, because diethyl acetal is a high boiling point organic relative to other organics formed during hydrogenation. Further applications for ethanol in as an ethanol industrial and a fuel grade ethanol may require reduced concentrations of diethyl acetal, e.g., less than 1 wt. % diethyl acetal, less than 0.1 wt. % diethyl acetal or less than 0.01 wt. % diethyl acetal. In terms of ranges, the diethyl acetal may be from 0.0001 to 1 wt. %, e.g., from 0.0001 to 0.1 wt. % or from 0.0001 to 0.01 wt. %.

The present invention provides processes for reducing acetal concentrations during the recovery of ethanol. Without being bound by theory, the present invention may enhance the equilibrium to favor hydrolysis of acetal or to reduce the acetalization towards the formation of acetal. In one embodiment, from 10 to 75% of the acetal may be decomposed in column at increased pressure, e.g., from 15 to 60% or more preferably from 20 to 40%.

In one embodiment, acetal concentrations may be decreased by separating the crude mixture, or a derivative stream thereof, in a distillation column that is operated at an increased pressure. In separating ethanol from the crude mixture, there may be several distillation columns and acetal concentration may be reduced by operating at least one of the several distillation columns at an increased pressure. The increased pressure in the column may reduce the acetal concentration. The pressure may increase depending on the concentration of acetal concentration fed to the column. In one embodiment, the increased pressure is greater than atmospheric pressure, e.g., from 101 kPa to 5,000 kPa, e.g., from 120 kPa to 4,000 kPa, or from 150 kPa to 3,000 kPa.

In some embodiments, one of the columns in the separation may be operated at a higher pressure than the other columns to further enhance acetal hydrolysis within that column.

As ethanol is recovered from the crude mixture, the acetal may form in any of the columns, thus it may be necessary to operate the last column in the separation process at an increased pressure. The remaining columns may be operated at any pressure as needed to further separate ethanol. For example, low pressure or vacuum conditions may enhance separation of ethyl acetate and ethanol.

In another embodiment, acetal concentration may be decreased by separating ethanol from the crude mixture, or derivative stream thereof, in a distillation column that has a stripping section of at least 40 stages, e.g., at least 50 stages or at least 60 stages. Preferably, ethanol is recovered in the residue of such a column. The distillation column having this stripping section may also be operated at an increased pressure to further reduce acetal concentrations.

In addition to diethyl acetal, embodiments of the present invention may also hydrolyze other acetals, such as those selected from the group consisting of ethyl propyl acetal, ethyl butyl acetal, dimethyl acetal, methyl ethyl acetal, and hemiacetals and mixtures thereof.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol mixture may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehydes and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the reactor. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a mole percentage based on acetic acid in the feed. As indicated above, the conversion for the first embodiment is from 40% to 70%, and the conversion for the second embodiment is greater than 85%.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, in the reactor, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol mixture produced by the reactor, before any subsequent processing, such as purification and separation, will typically comprise acetic acid, ethanol and water. As used herein, the term "crude ethanol mixture" refers to any composition comprising from 5 to 70 wt. % ethanol and from 5 to 40 wt. % water. Exemplary compositional ranges for the crude ethanol mixture are provided in Table 1. The "others" identified in Table 1 may include, for example, esters, ethers, aldehydes, ketones, alkanes, and carbon dioxide.

TABLE 1

CRUDE ETHANOL MIXTURE COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 5 to 70 | 5 to 50 |
| Water | 5 to 30 | 5 to 28 | 10 to 26 | 10 to 22 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Diethyl Acetal | 0.001 to 5 | 0.01 to 3 | 0.1 to 2 | 0.5 to 1.5 |
| Others | 0.1 to 10 | 0.1 to 6 | 0.1 to 4 | — |

In one embodiment, the crude ethanol mixture may comprise acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Ethanol Separation

Ethanol produced may be recovered using several different techniques. In FIG. 1, the separation of the crude ethanol mixture uses four columns. In one embodiment, the first column 120, second column 123, and/or third column 128 may be operated at an increased pressure. In one embodiment, second column 123 may have a stripping section comprising at least 40 stages, e.g., at least 50 stages or at least 60 stages.

Figure 2:
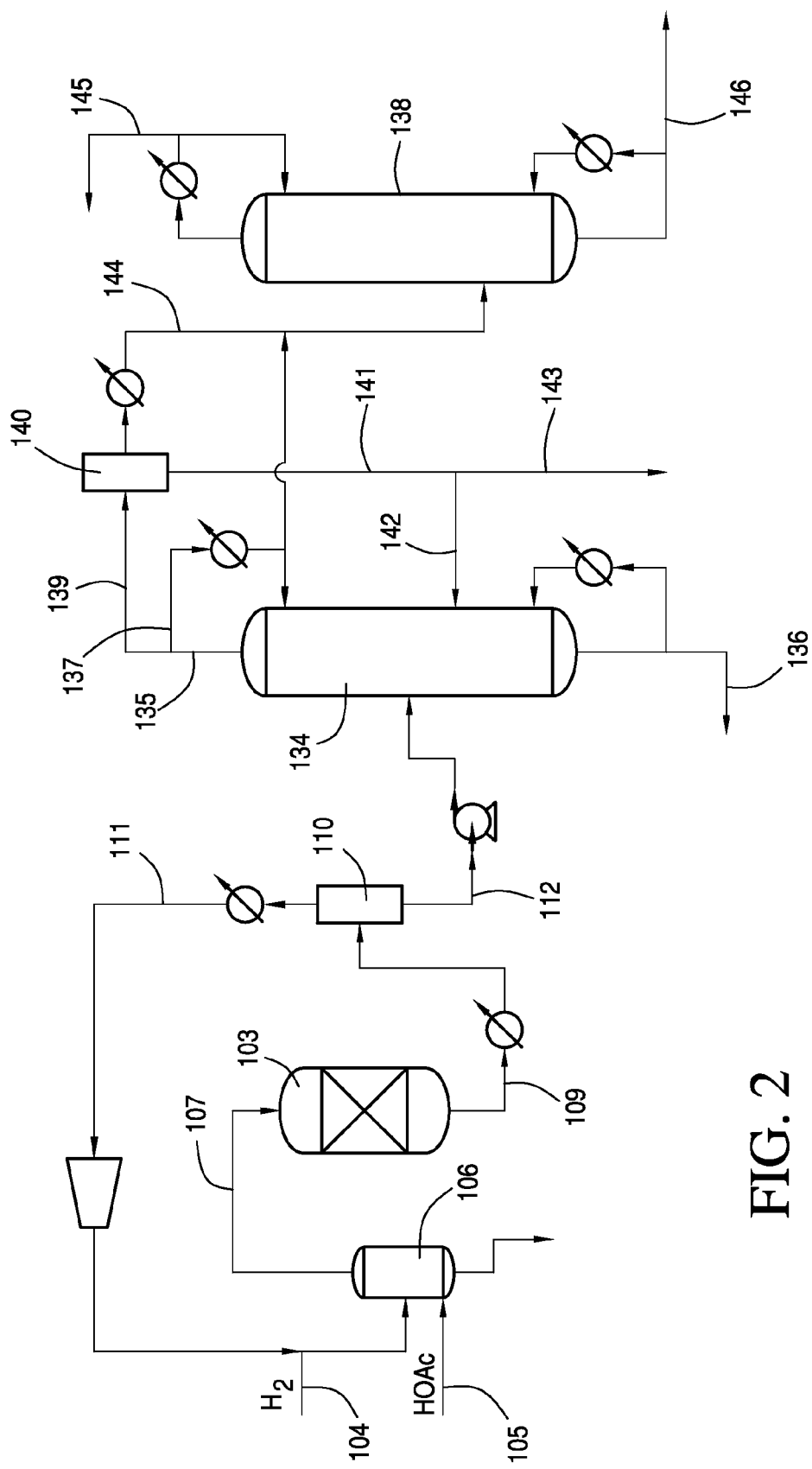
FIG. 2 is a schematic diagram of another hydrogenation process having two columns with an intervening water separation in accordance with an embodiment of the present invention.
Figure 3:
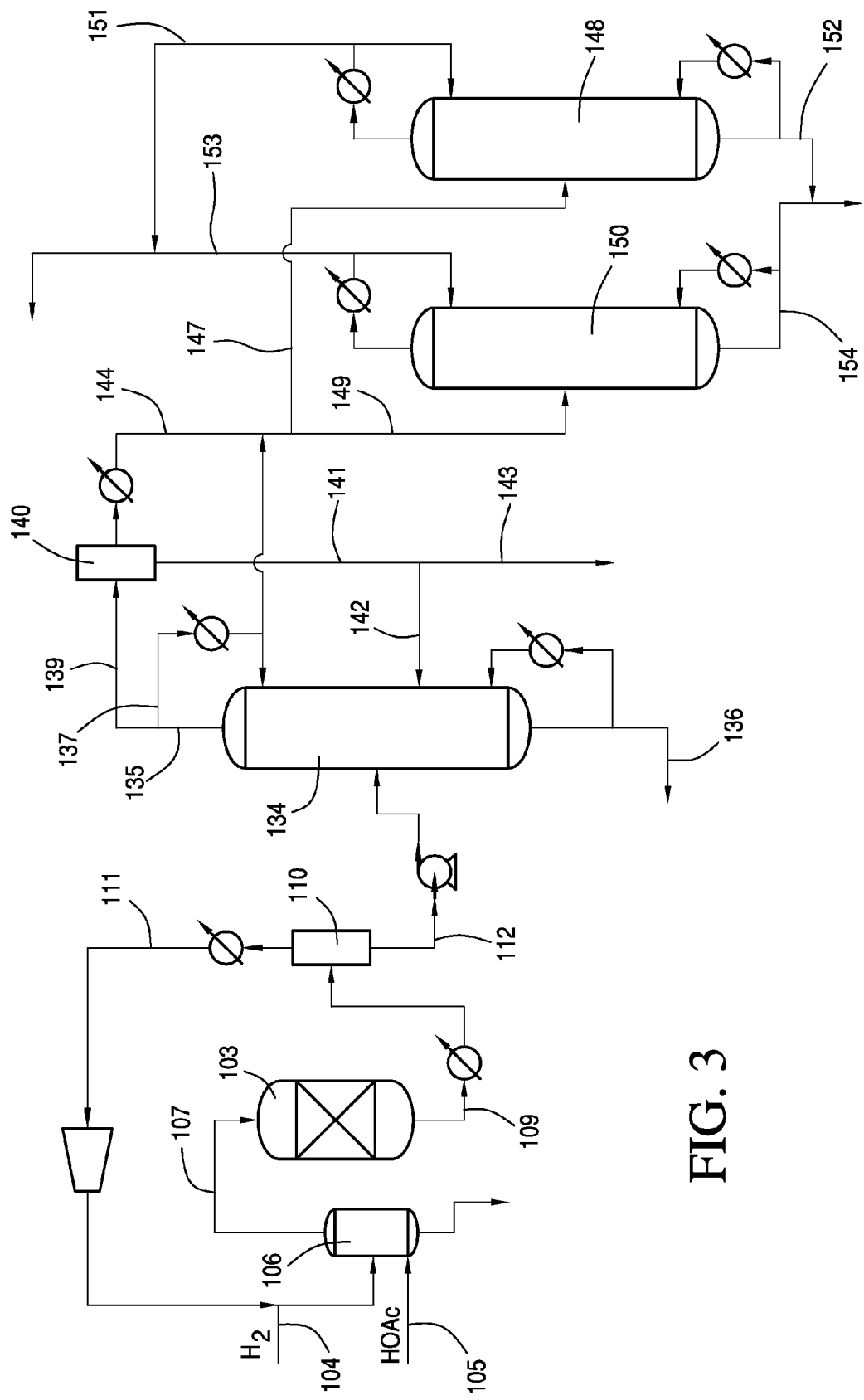
FIG. 3 is a schematic diagram having the intervening water separation of FIG. 2 with parallel high and low pressure columns in accordance with an embodiment of the present invention.
Figure 4:
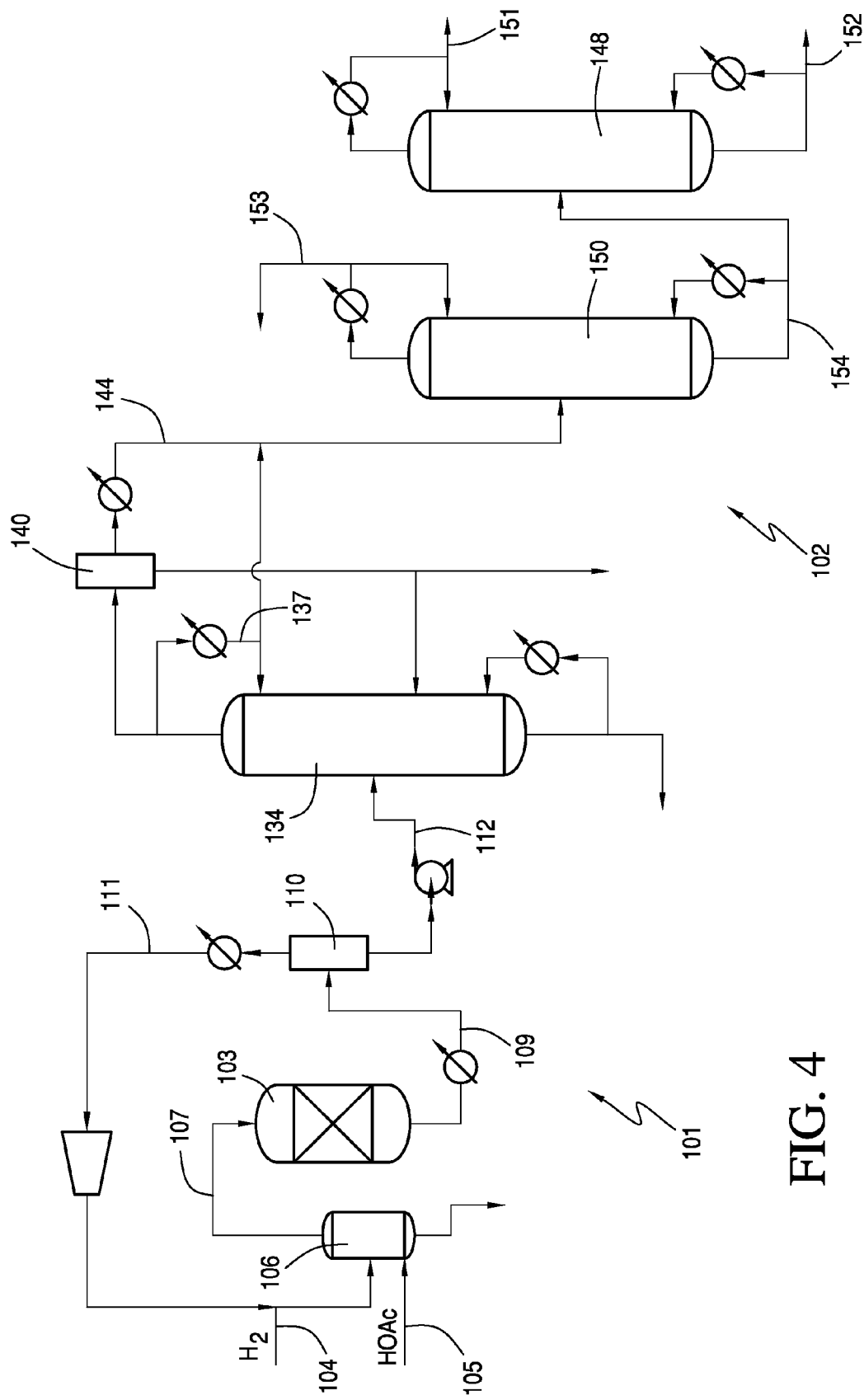
FIGS. 4 and 5 are schematic diagrams having the intervening water separation of FIG. 2 with high and low pressure columns in series in accordance with an embodiment of the present invention.
Figure 5:
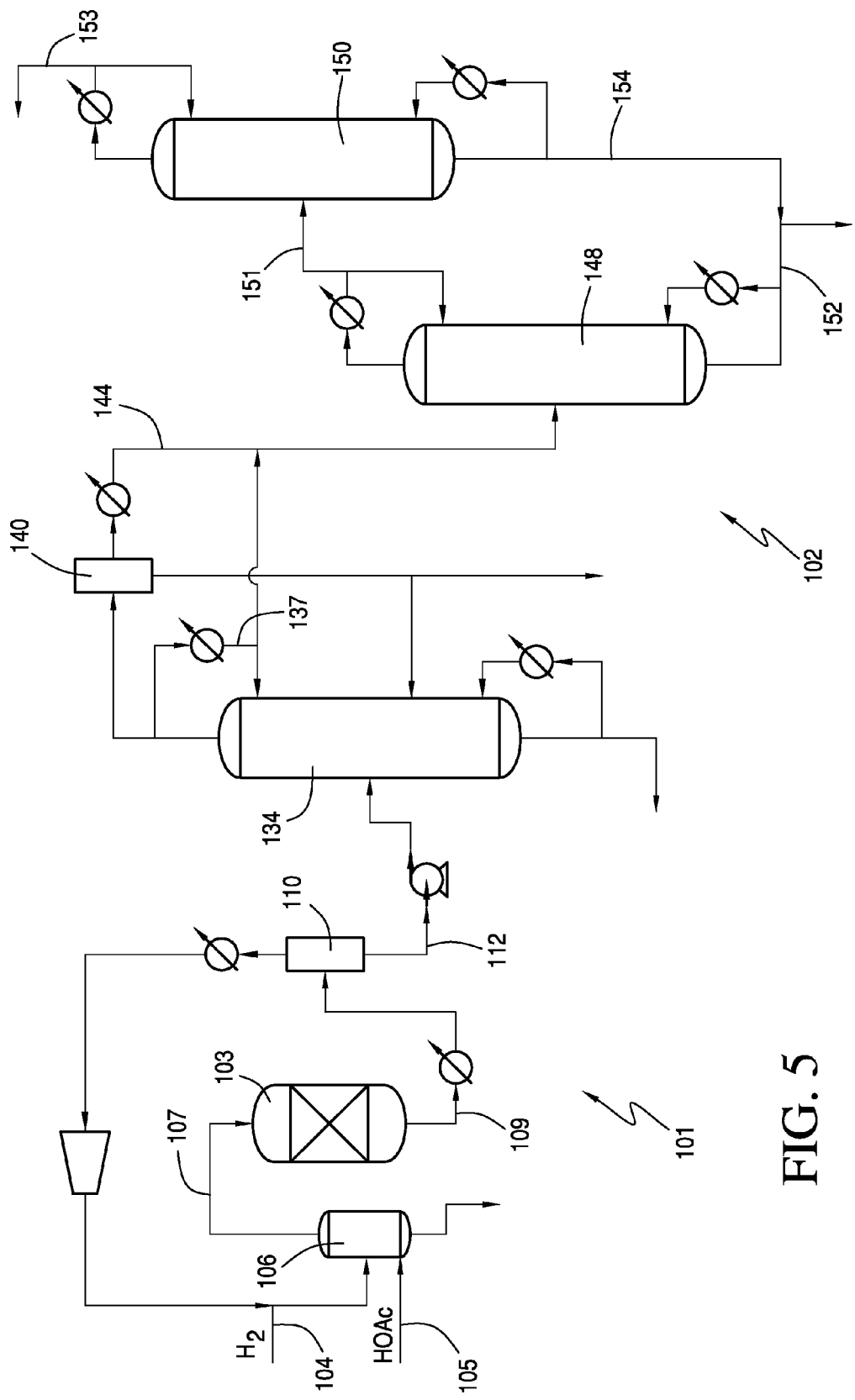

In FIG. 2, the crude ethanol mixture is separated in two columns with an intervening water separation. Either column in FIG. 2 may be operated an increased pressure. FIG. 3 is similar separation as FIG. 2, except ethanol containing stream is separated in parallel using a column operating at vacuum conditions and a column operating at an increased pressure. FIG. 4 separates an ethanol containing stream in series using a low pressure column, followed by a column operating at an increased pressure. FIG. 5 separates an ethanol containing stream in series using a column operating at an increased pressure followed by separating the distillate in a low pressure column. In FIGS. 4 and 5, the residue of the low pressure column may be combined with the residue of the column operated at an increased pressure to form an ethanol product.

Figure 6:
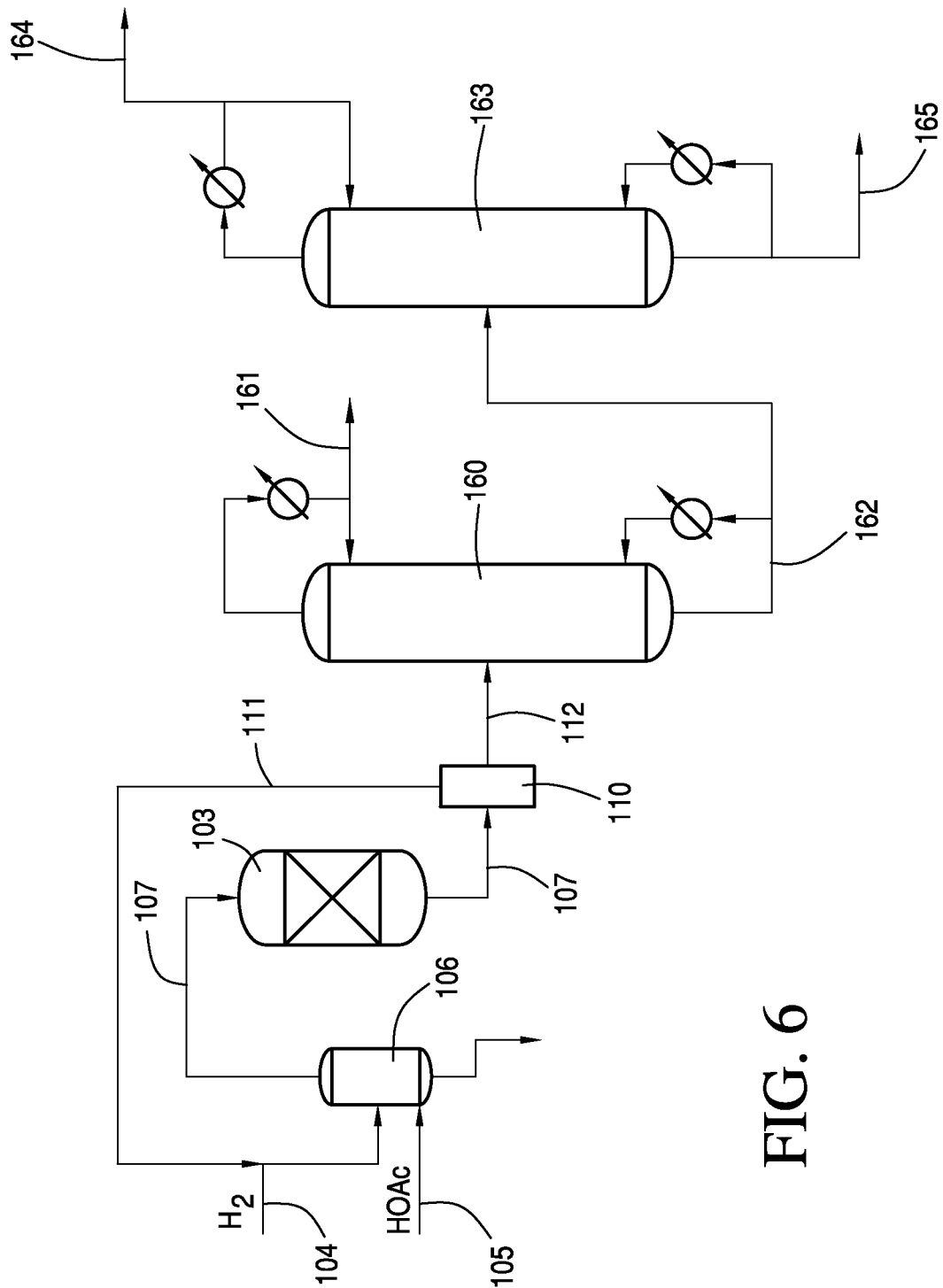
FIG. 6 is a schematic diagram of another hydrogenation process having two columns in accordance with an embodiment of the present invention.

In FIG. 6, the separation of the crude ethanol mixture uses two columns. Either column in FIG. 6 may be operated an increased pressure, but it may be preferred to operate the first column 170 at a higher pressure.

Other separation systems may also be used with embodiments of the present invention. For purposes of convenience, the columns in each exemplary separation processes, may be referred as the first column, second columns, third columns, etc.

In each of the FIGS., hydrogenation system 100 includes a reaction zone 101, and separation zone 102. Hydrogen and acetic acid via lines 104 and 105, respectively, are fed to a vaporizer 106 to create a vapor feed stream in line 107 that is directed to reactor 103. In one embodiment, lines 104 and 105 may be combined and jointly fed to the vaporizer 106. The temperature of the vapor feed stream in line 107 is preferably from 100° C. to 350° C., e.g., from 120° C. to 310° C. or from 150° C. to 300° C. Any feed that is not vaporized is removed from vaporizer 106 and may be recycled or discarded thereto. In addition, although line 107 is shown as being directed to the top of reactor 103, line 107 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of the vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol mixture stream is withdrawn, preferably continuously, from reactor 103 via line 109.

The crude ethanol mixture stream in line 109 may be condensed and fed to a separator 110, which, in turn, provides a vapor stream 111 and a liquid stream 112. In some embodiments, separator 110 may comprise a flasher or a knockout pot. The separator 110 may operate at a temperature of from 20° C. to 250° C., e.g., from 30° C. to 225° C. or from 60° C. to 200° C. The pressure of separator 110 may be from 50 kPa to 2000 kPa, e.g., from 75 kPa to 1500 kPa or from 100 kPa to 1000 kPa. Optionally, the crude ethanol mixture in line 109 may pass through one or more membranes to separate hydrogen and/or other non-condensable gases.

The vapor stream 111 exiting separator 110 may comprise hydrogen and hydrocarbons, and may be purged and/or returned to reaction zone 101. When returned to reaction zone 101, vapor stream 110 is combined with the hydrogen feed 104 and co-fed to vaporizer 106. In some embodiments, the returned vapor stream 111 may be compressed before being combined with hydrogen feed 104.

In FIG. 1, the liquid stream 112 from separator 110 is withdrawn and pumped to the side of first column 120, also referred to as an "acid separation column." In one embodiment, the contents of liquid stream 112 are substantially similar to the crude ethanol mixture obtained from the reactor, except that the composition has been depleted of hydrogen, carbon dioxide, methane and/or ethane, which are removed by separator 110. Accordingly, liquid stream 112 may also be referred to as a crude ethanol mixture. Exemplary components of liquid stream 112 are provided in Table 2. It should be understood that liquid stream 112 may contain other components, not listed in Table 2.

TABLE 2

COLUMN FEED COMPOSITION (Liquid Stream 112)

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 5 to 70 |
| Water | 5 to 30 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol mixture in line 109 or in liquid stream 112 may be further fed to an esterification reactor, hydrogenolysis reactor, or combination thereof. An esterification reactor may be used to consume residual acetic acid present in the crude ethanol mixture to further reduce the amount of acetic acid that would otherwise need to be removed. Hydrogenolysis may be used to convert ethyl acetate in the crude ethanol mixture to ethanol.

In the embodiment shown in FIG. 1, line 112 is introduced in the lower part of first column 120, e.g., lower half or lower third. In first column 120, acetic acid, a portion of the water, and other heavy components, if present, are removed from the composition in line 121 and are withdrawn, preferably continuously, as residue. Some or all of the residue may be returned and/or recycled back to reaction zone 101 via line 121. Recycling the acetic acid in line 121 to the vaporizer 106 may reduce the amount of heavies that need to be purged from vaporizer 106. Reducing the amount of heavies to be purged may improve efficiencies of the process while reducing byproducts.

First column 120 also forms an overhead distillate, which is withdrawn in line 122, and which may be condensed and refluxed, for example, at a ratio of from 10:1 to 1:10, e.g., from 3:1 to 1:3 or from 1:2 to 2:1. The distillate in line 122 comprises primarily ethanol, as well as water, ethyl acetate, acetaldehyde, and/or diethyl acetal. For example, distillate may comprise from 20 to 75 wt. % ethanol and 10 to 40 wt. % ethanol. Preferably, the concentration of acetic acid in the distillate is less than 2 wt. %, e.g., less than 1 wt. % or less than 0.5 wt. %.

In one embodiment, column 120 may operate at an increased pressure of above atmospheric pressure to enhance the hydrolysis of acetal fed to column 120. When column 120 is operated at increased pressure, the concentration of diethyl acetal in the first distillate in line 121 may be less than 1 wt. %, e.g., less than 0.1 wt. % or less than 0.01 wt. %.

When another column the purification section 102 of FIG. 1, is operated at an increased pressure, first column 120 may be operated at ambient pressure. In other embodiments, the pressure of first column 120 may range from 0.1 kPa to 510 kPa, e.g., from 1 kPa to 475 kPa or from 1 kPa to 375 kPa. When first column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C.

In one embodiment, even without operating first column 120 under increased pressure, without being bound by theory, it has surprisingly and unexpectedly been discovered that when any amount of acetal is detected in the feed, the acetal appears to decompose in the column such that less or even no detectable amounts are present in the distillate and/or residue. Increasing the pressure of first column 120 may further reduce the concentrations of acetal. In one embodiment, from 10 to 75% of the diethyl acetal may be decomposed in first column 120, e.g., from 15 to 60% or more preferably from 20 to 40%.

To further separate distillate, line 122 is introduced to the second column 123, also referred to as the "light ends column," preferably in the middle part of column 123. Preferably the second column 123 is an extractive distillation column, and an extraction agent is added thereto via lines 124 and/or 125. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 122 that is fed to the second column 123 comprises ethanol, water, and ethyl acetate. These compounds tend to form binary and ternary azeotropes, which decrease separation efficiency. As shown, in one embodiment the extraction agent comprises the third residue in line 124. Preferably, the recycled third residue in line 124 is fed to second column 123 at a point higher than the first distillate in line 122. In one embodiment, the recycled third residue in line 124 is fed near the top of second column 123 or fed, for example, above the feed in line 122 and below the reflux line from the condensed overheads. In a tray column, the third residue in line 124 is continuously added near the top of the second column 123 so that an appreciable amount of the third residue is present in the liquid phase on all of the trays below. In another embodiment, the extraction agent is fed from a source outside of the process 100 via line 125 to second column 123. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 124 and co-fed to the second column 123. The additional extraction agent may also be added separately to the second column 123. In one aspect, the extraction agent comprises an extraction agent, e.g., water, derived from an external source via line 125 and none of the extraction agent is derived from the third residue.

Second column 123 may be a tray or packed column. In one embodiment, second column 123 is a tray column having from 5 to 120 trays, e.g., from 15 to 80 trays or from 20 to 70 trays. In one embodiment, the stripping section of the second column 123 may have at least 40 stages, e.g. at least 50 stages or at least 60 stages. As indicated above, the increased stripping section of second column 123 may enhance hydrolysis of diethyl acetal.

In FIG. 1, second column 123 may operate at an increased pressure, i.e. greater than atmospheric pressure. In other embodiments, when either the first column 123 or third column 128 is operated at increased pressure, the pressure of second column 123 may range from 0.1 kPa to 510 kPa, e.g., from 1 kPa to 475 kPa or from 1 kPa to 375 kPa.

The temperature of second column 123 at atmospheric pressure may vary. In one embodiment second residue exiting in line 126 preferably is at a temperature from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C.

The second residue in line 126 comprises ethanol and water. The second residue may comprise less than 3 wt. % ethyl acetate, e.g., less than 1 wt. % ethyl acetate or less than 0.5 wt. % ethyl acetate. The second distillate in line 127 comprises ethyl acetate, acetaldehyde, and/or diethyl acetal. In addition, minor amounts of ethanol may be present in the second distillate. The weight ratio of ethanol in the second residue to second distillate preferably is at least 3:1, e.g., at least 6:1, at least 8:1, at least 10:1 or at least 15:1.

All or a portion of the third residue is recycled to the second column. In one embodiment, all of the third residue may be recycled until process 100 reaches a steady state and then a portion of the third residue is recycled with the remaining portion being purged from the system 100. The composition of the second residue will tend to have lower amounts of ethanol than when the third residue is not recycled. As the third residue is recycled, the composition of the second residue comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 1, for example, at a reflux ratio of from 1:10 to 10:1, e.g., from 1:3 to 3:1 or from 1:2 to 2:1. The third residue in line 124, which comprises primarily water, preferably is returned to the second column 123 as an extraction agent as described above. In one embodiment, a first portion of the third residue in line 124 is recycled to the second column and a second portion is purged and removed from the system via line 130. In one embodiment, once the process reaches steady state, the second portion of water to be purged is substantially similar to the amount of water formed in the hydrogenation of acetic acid. In one embodiment, a portion of the third residue may be used to hydrolyze any other stream, such as one or more streams comprising ethyl acetate. In one embodiment, the third residue in line 124 is withdrawn from third column 128 at a temperature higher than the operating temperature of the second column 123. Preferably, the third residue in line 124 is integrated to heat one or more other streams or is reboiled prior to be returned to the second column 123.

Although FIG. 1 show third residue being directly recycled to second column 123, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 128 is preferably a tray column. In one embodiment, third column 128 may operate at an increased pressure to reduce diethyl acetal concentration. When either first column 120 or second column 123 is operated at increased pressure, third column may be operated from 0.1 kPa to 510 kPa, e.g., from 1 kPa to 475 kPa or from 1 kPa to 375 kPa.

At atmospheric pressure, the temperature of the third distillate exiting in line 129 preferably is from 60° C. to 110° C., e.g., from 70° C. to 100° C. or from 75° C. to 95° C. The temperature of the third residue in line 124 preferably is from 70° C. to 115° C., e.g., from 80° C. to 110° C. or from 85° C. to 105° C.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 128. The impurities may be purged and/or retained within the system 100. The ethanol product obtained from third distillate in FIG. 1, is shown below in Table 3. Preferably, the ethanol product comprises less than 1 wt. % diethyl acetal, e.g., less than 0.5 wt. % or less than 0.01 wt. %.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

In FIG. 1, any of first column 120, second column 123, or third column 128 may be operated at increased pressure, e.g., from 101 kPa to 5,000 kPa, e.g., from 120 kPa to 4,000 kPa, or from 150 kPa to 3,000 kPa. Preferably, at least second column 123 is operated at increased pressure. In some embodiments two of the columns may be operated at increased pressure, such as the second column 123 and third column 128.

Returning to second column 123, the second distillate preferably is refluxed as shown in FIG. 1, at a reflux ratio of 1:10 to 10:1, e.g., from 1:5 to 5:1 or from 1:3 to 3:1. The second distillate in line 127 may be purged or recycled to the reaction zone. The second distillate in line 127 may be further processed in an optional fourth column 131, also referred to as the "acetaldehyde removal column." In optional fourth column 131 the second distillate is separated into a fourth distillate, which comprises acetaldehyde, in line 132 and a fourth residue, which comprises ethyl acetate, in line 133. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101. For example, the fourth distillate may be combined with the acetic acid feed, added to the vaporizer 106, or added directly to the reactor 103. The fourth distillate preferably is co-fed with the acetic acid in feed line 105 to vaporizer 106. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of optional fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Optional fourth column 131 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 131 may operate at a pressure that is higher than the pressure of the other columns. Although acetal hydrolysis may be enhanced at increased pressure in optional fourth column 131, because no ethanol is recovered from optional fourth column 131 the increased pressure may have little effect on the diethyl acetal concentration in the ethanol product.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C.

In one embodiment, a portion of the third residue in line 124 is recycled to second column 123. In one embodiment, recycling the third residue further reduces the aldehyde components in the second residue and concentrates these aldehyde components in second distillate in line 127 and thereby sent to the fourth column 131, wherein the aldehydes may be more easily separated. The third distillate, e.g. intermediate stream, in line 129 may have lower concentrations of aldehydes and esters due to the recycling of third residue in line 124.

FIG. 2 illustrates another exemplary separation system that has a similar reaction zone 101 as FIG. 1 and produces a liquid stream 112, e.g., crude ethanol mixture, for further separation. In one preferred embodiment, the reaction zone 101 of FIG. 2 operates at above 70% acetic acid conversion, e.g., above 85% conversion or above 90% conversion. Thus, the acetic acid concentration in the liquid stream 112 may be low.

Liquid stream 112 is fed to the first column 134 to yield a first distillate 135 and first residue 136. Liquid stream 112 may be introduced in the middle or lower portion of first column 134, also referred to as acid-water column. In one embodiment, no entrainers are added to first column 134. Water and acetic acid, along with any other heavy components, if present, are removed from liquid stream 112 and are withdrawn, preferably continuously, as a first residue in line 136. Preferably, a substantial portion of the water in the crude ethanol mixture that is fed to first column 134 may be removed in the first residue, for example, up to about 75% or to about 90% of the water from the crude ethanol mixture. In one embodiment, 30 to 90% of the water in the crude ethanol mixture is removed in the residue, e.g., from 40 to 88% of the water or from 50 to 84% of the water.

First column 134 may be operated under increased pressure to enhance diethyl acetal separation. When column 134 is operated under about 170 kPa, the temperature of the residue exiting in line 136 preferably is from 90° C. to 130° C., e.g., from 95° C. to 120° C. or from 100° C. to 115° C. The temperature of the distillate exiting in line 135 preferably is from 60° C. to 90° C., e.g., from 65° C. to 85° C. or from 70° C. to 80° C. In some embodiments, the pressure of first column 134 may also range from 0.1 kPa to 510 kPa, e.g., from 1 kPa to 475 kPa or from 1 kPa to 375 kPa.

The first distillate in line 135 comprises water, in addition to ethanol and other organics. In terms of ranges, the water concentration in the first distillate in line 135 preferably is from 4 wt. % to 38 wt. %, e.g., from 7 wt. % to 32 wt. %, or from 7 to 25 wt. %. A portion of first distillate in line 137 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 134. The condensed portion of the first distillate may also be fed to a second column 138.

The remaining portion of the first distillate in line 139 is fed to a water separation unit 140. Water separation unit 140 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 140 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separator 140 may remove at least 95% of the water from the portion of first distillate in line 139, and more preferably from 99% to 99.99% of the water from the first distillate, in a water stream 141. All or a portion of water stream 141 may be returned to first column 134 in line 142, where the water preferably is ultimately recovered from column 134 in the first residue in line 136. Additionally or alternatively, all or a portion of water stream 141 may be purged via line 143. The remaining portion of first distillate exits the water separator 140 as ethanol mixture stream 144. Ethanol mixture stream 144 may have a low water concentration of less than 10 wt. %, e.g., less than 6 wt. % or less than 2 wt. %.

Preferably, ethanol mixture stream 144 is not returned or refluxed to first column 135. The condensed portion of the first distillate in line 137 may be combined with ethanol mixture stream 144 to control the water concentration fed to the second column 138. For example, in some embodiments the first distillate may be split into equal portions, while in other embodiments, all of the first distillate may be condensed or all of the first distillate may be processed in the water separation unit. In FIG. 2, the condensed portion in line 137 and ethanol mixture stream 144 are co-fed to second column 138. In other embodiments, the condensed portion in line 137 and ethanol mixture stream 144 may be separately fed to second column 138. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 138 in FIG. 2, also referred to as the "light ends column," removes ethyl acetate and acetaldehyde from the first distillate in line 137 and/or ethanol mixture stream 144. Ethyl acetate and acetaldehyde are removed as a second distillate in line 145 and ethanol is removed as the second residue in line 146. Preferably ethanol is recovered with low amounts of ethyl acetate, acetaldehyde, and/or acetal, e.g., less than 1 wt. % or more preferably less than 0.5 wt. %. The ethanol product obtained from second residue in FIG. 2, is shown below in Table 3. Preferably, the ethanol product comprises less than 1 wt. % diethyl acetal, e.g., less than 0.5 wt. % or less than 0.01 wt. %.

Second column 138 may be a tray column or packed column. In one embodiment, second column 138 is a tray column having from 5 to 120 trays, e.g., from 15 to 100 trays or from 20 to 90 trays. In one embodiment, there may be at least 40 stages in the stripping section of second column 138, e.g., at least 50 stages or at least 60 stages. The additional stages in stripping section may enhance acetal hydrolysis.

In one embodiment, second column 138 operates at an increased pressure from 101 kPa to 5,000 kPa, e.g., from 120 kPa to 4,000 kPa, or from 150 kPa to 3,000 kPa. The increased pressure in second column 138 may further enhance acetal, in particular diethyl acetal, hydrolysis in second column 138. When first column 134 operates at increased pressure, the second column 138 may operate at a pressure ranging from 0.1 kPa to 510 kPa, e.g., from 10 kPa to 450 kPa or from 50 kPa to 350 kPa. Although the temperature of second column 138 may vary, when at about 20 kPa to 70 kPa, the temperature of the second residue exiting in line 146 preferably is from 30° C. to 75° C., e.g., from 35° C. to 70° C. or from 40° C. to 65° C. The temperature of the second distillate exiting in line 145 preferably is from 20° C. to 55° C., e.g., from 25° C. to 50° C. or from 30° C. to 45° C.

The total concentration of water fed to second column 138 preferably is less than 10 wt. %, as discussed above. When first distillate in line 137 and/or ethanol mixture stream 144 comprises minor amounts of water, e.g., less than 1 wt. % or less than 0.5 wt. %, additional water may be fed to the second column 138 as an extractive agent in the upper portion of the column. A sufficient amount of water is preferably added via the extractive agent such that the total concentration of water fed to second column 138 is from 1 to 10 wt. % water, e.g., from 2 to 6 wt. %, based on the total weight of all components fed to second column 138. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

The second distillate in line 145, which comprises ethyl acetate and/or acetaldehyde, preferably is refluxed as shown in FIG. 2, for example, at a reflux ratio of from 1:30 to 30:1, e.g., from 1:10 to 10:1 or from 1:3 to 3:1. In one aspect, not shown, the second distillate 145 or a portion thereof may be returned to reactor 103.

In one embodiment, the second distillate in line 145 and/or a refined second distillate, or a portion of either or both streams, may be further separated to produce an acetaldehyde-containing stream and an ethyl acetate-containing stream. For example, the optional fourth column 131 of FIG. 1 may be used to separate second distillate in line 145. This may allow a portion of either the resulting acetaldehyde-containing stream or ethyl acetate-containing stream to be recycled to reactor 103 while purging the other stream. The purge stream may be valuable as a source of either ethyl acetate and/or acetaldehyde.

In one embodiment, it may be preferred to operate second column 138 in FIG. 2 at a pressure less than atmospheric pressure to decrease the energy required to separate ethyl acetate and ethanol. However, the decreased pressure may not have the advantage of enhancing diethyl acetal hydrolysis. FIG. 3 shows process similar to FIG. 2, except first distillate in line 137 and/or ethanol mixture stream 144 is split and a first portion is fed via line 147 to a high pressure second column 148, and a second portion is fed via line 149 to a low pressure second column 150. The relative amounts fed to the high pressure second column 148 and low pressure second column 150 may be controlled based on the concentration of diethyl acetal and/or ethyl acetate in the ethanol containing residue. When diethyl acetal concentrations in the ethanol containing residue increase a larger portion of first distillate in line 137 and/or ethanol mixture stream 144 may be fed to line 147. Likewise, when ethyl acetate concentrations increase, a larger portion may be fed to low pressure second column 150 via line 149. A control valve may be used to regulate the flow between the first and second portions.

In FIG. 3, high pressure second column 148 operates at an increased pressure above atmospheric pressure to yield a distillate comprising ethyl acetate, acetaldehyde, and diethyl acetal in line 151 and a residue comprising ethanol in line 152. In one embodiment residue in line 152 contains low concentrations of diethyl acetal, e.g., less than 1 wt. %, or less than 0.5 wt. %. High pressure second column 148 may also have an increased stripping section of at least 40 stages, e.g., at least 50 stages or at least 60 stages.

Low pressure second column 150 operates at in a vacuum or a pressure less than atmospheric pressure, e.g., less than 70 kPa or less than 50 kPa. In terms of second the low pressure second column 150 may operate from 0.1 to 100 kPa, e.g. from 0.1 to 70 kPa, or from 0.1 to 35 kPa. The decreased pressure may further enhance separation of ethyl acetate and ethanol. Low pressure second column 150 also yield a distillate comprising ethyl acetate, acetaldehyde, and diethyl acetal in line 153 and a residue comprising ethanol in line 154. In one embodiment residue in line 154 contains low concentrations of ethyl acetate, e.g., less than 1 wt. %, or less than 0.5 wt. %.

The distillates of each column may be combined and returned to the reactor 103 in a similar manner as discussed above in FIG. 2. In addition, the residues of each column in FIG. 3, may be combined to produce an ethanol product. In some embodiments, it may be desired to produce separate ethanol products from each of the second columns 148 and 150 in FIG. 3.

FIG. 3 illustrates high and low pressure columns in parallel. In some embodiments, it may be necessary to operate the high and low pressure columns in series. FIG. 4 illustrates a process where the first distillate in line 137 and/or ethanol mixture stream 144 is initially fed to the low pressure second column 150. As indicated above the residue in line 154 may have low concentrations of ethyl acetate, but may also have higher concentrations of diethyl acetal. The residue in line 154 is fed to a high pressure second column 148 to enhance hydrolysis of diethyl acetal. In high pressure second column 148, diethyl acetal is hydrolyzed to yield a distillate in line 151 comprising acetaldehyde and a residue in line 152 comprising ethanol. Using the high pressure second column 148, at least 20% of the diethyl acetal in residue in line 154 may be hydrolyzed, e.g., at least 30% or at least 50%. Thus, the concentration of diethyl acetal in residue in line 152 may be less than 1 wt. %, e.g., less than 0.5 wt. %.

FIG. 5 reverses the order of the low pressure second column 150 and high pressure second column 148 from FIG. 4. FIG. 5 illustrates a process where the first distillate in line 137 and/or ethanol mixture stream 144 is initially fed to the high pressure second column 148. As indicated above the residue in line 152 may have low concentrations of diethyl acetal, but may also have higher concentrations of ethyl acetate. In high pressure second column 148, diethyl acetal is hydrolyzed to yield a distillate in line 151 and a residue in line 152 comprising ethanol. The distillate in line 151 is fed to a low pressure second column 150. Distillate in line 151 may comprise ethyl acetate and ethanol and it may be desirable to recover the ethanol instead of recycling the ethanol to reactor 103. Using low pressure second column 150, any ethanol in distillate in line 151 is separated as the residue in line 154 and the ethyl acetate is removed as the distillate in line 153.

Distillate in line 153 is recycled to reactor 103. Residue in line 154 may be combined with residue in line 152 to form an ethanol product. In some embodiments, each of the residue streams may be used as separated ethanol products.

Returning to FIG. 2, pressure of the second column 138 may be changed depending on the concentration of the diethyl acetal in the second residue in line 146. As the diethyl acetal concentration increases in the second residue in line 146 above, for example, 1 wt. %, the pressure of second column 138 may also be increased. In addition, when ethyl acetate concentration in the second residue in line 146 above, for example, 1 wt. %, the pressure of second column 138 may be decreased. This allows second column 138 to be adjusted as necessary without additional capital for a further distillation column.

In another embodiment, the liquid stream 112 from reaction zone 103 may be separated used a process as shown in FIG. 6. In one preferred embodiment, reaction zone 101 of FIG. 6 operates at above 80% acetic acid conversion, e.g., above 90% conversion or above 99% conversion. Thus, the acetic acid concentration in the liquid stream 112 may be low.

In the exemplary embodiment shown in FIG. 6, liquid stream 112 is introduced in the upper part of first column 160, e.g., upper half or upper third. In one embodiment, no entrainers are added to first column 160. In first column 160, a weight majority of the ethanol, water, acetic acid, and other heavy components, if present, are removed from liquid stream 112 and are withdrawn, preferably continuously, as residue in line 162. First column 160 also forms an overhead distillate, which is withdrawn in line 161, and which may be condensed and refluxed, for example, at a ratio of from 30:1 to 1:30, e.g., from 10:1 to 1:10 or from 1:5 to 5:1. The first distillate in line 161 preferably comprises a weight majority of the ethyl acetate from liquid line 112. In addition, distillate in line 161 may also comprise acetaldehyde.

In one embodiment, first column 160 may be operated at an increased pressure to enhance diethyl acetal hydrolysis. In addition, first column 160 may also have a stripping section that comprises at least 40 stages, e.g., at least 50 stages or at least 60 stages.

When column 160 is operated under about 170 kPa, the temperature of the residue exiting in line 162 preferably is from 70° C. to 155° C., e.g., from 90° C. to 130° C. or from 100° C. to 110° C. The base of column 160 may be maintained at a relatively low temperature by withdrawing a residue stream comprising ethanol, water, and acetic acid, thereby providing an energy efficiency advantage. The temperature, at 170 kPa, of the distillate exiting in line 161 preferably is from 75° C. to 100° C., e.g., from 75° C. to 83° C. or from 81° C. to 84° C.

In some embodiments, when the second column 163 of FIG. 6 is operated at an increased pressure, the pressure of first column 170 may range from 0.1 kPa to 510 kPa, e.g., from 1 kPa to 475 kPa or from 1 kPa to 375 kPa.

In an embodiment of the present invention, column 160 of FIG. 6 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 162 to water in the distillate in line 161 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 ppm, less than 500 ppm or less than 100 ppm acetic acid. The distillate may be purged from the system or recycled in whole or part to reactor 103. In some embodiments, the distillate may be further separated, e.g., in an optional fourth column of FIG. 1, into an acetaldehyde stream and an ethyl acetate stream. Either of these streams may be returned to the reactor 103 or separated from system 100 as a separate product.

To recover ethanol, the residue in line 162 may be further separated in a second column 163, also referred to as an "acid separation column." An acid separation column may be used when the acetic acid concentration in the first residue is greater than 1 wt. %, e.g., greater than 5 wt. %. The first residue in line 162 is introduced to second column 163 preferably in the top part of column 163, e.g., top half or top third. Second column 163 yields a second residue in line 165 comprising acetic acid and water, and a second distillate in line 164 comprising ethanol.

Second column 163 may be a tray column or packed column. In one embodiment, second column 163 is a tray column having from 5 to 150 trays, e.g., from 15 to 50 trays or from 20 to 45 trays. Similar to first column 160, second column may have a stripping section of at least 40 stages, e.g., at least 50 stages or at least 60 stages.

In one embodiment, second column 163 may be operated at an increased pressure to enhance diethyl acetal hydrolysis. In FIG. 6, it is more preferred to operate the first column 160 at an increased pressure, because second column 163 comprises very low amounts of acetaldehyde and/or acetals. Generally, the pressure of second column 163 may range from 0.1 kPa to 510 kPa, e.g., from 1 kPa to 475 kPa or from 1 kPa to 375 kPa. At atmospheric pressure the temperature of the second residue exiting in line 165 preferably is from 95° C. to 130° C., e.g., from 100° C. to 125° C. or from 110° C. to 120° C. The temperature of the second distillate exiting in line 164 preferably is from 60° C. to 105° C., e.g., from 75° C. to 100° C. or from 80° C. to 100° C.

The weight ratio of ethanol in the second distillate in line 164 to ethanol in the second residue in line 165 preferably is at least 35:1. In one embodiment, the weight ratio of water in the second residue 165 to water in the second distillate 164 is greater than 2:1, e.g., greater than 4:1 or greater than 6:1. In addition, the weight ratio of acetic acid in the second residue 165 to acetic acid in the second distillate 164 preferably is greater than 10:1, e.g., greater than 15:1 or greater than 20:1. Preferably, the second distillate in line 164 is substantially free of acetic acid and may only contain, if any, trace amounts of acetic acid. Preferably, the second distillate in line 164 contains substantially no ethyl acetate.

The remaining water from the second distillate in line 164 may be removed in further embodiments of the present invention. Depending on the water concentration, the ethanol product may be derived from the second distillate in line 164. Some applications, such as industrial ethanol applications, may tolerate water in the ethanol product, while other applications, such as fuel applications, may require an anhydrous ethanol. The amount of water in the distillate of line 164 may be closer to the azeotropic amount of water, e.g., at least 4 wt. %, preferably less than 20 wt. %, e.g., less than 12 wt. % or less than 7.5 wt. %. Water may be removed from the second distillate in line 164 using several different separation techniques as described herein. Particularly preferred techniques include the use of distillation column, membranes, adsorption units, and combinations thereof.

Some of the residues withdrawn from the separation zone 102 comprise acetic acid and water. Depending on the amount of water and acetic acid contained in the residue of first column, for example first residue 120 in FIG. 1, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 103. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in figures may comprise any distillation column capable of performing the desired separation and/or purification. For example, other than the acid columns describe above, the other columns preferably are a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from a stream that primarily comprises ethanol from exemplary systems shown in the FIGURES. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 3.

TABLE 3

FINISHED ETHANOL COMPOSITIONS

| Component | Conc. (wt. %) | Conc. (wt. %) | Conc. (wt. %) |
| --- | --- | --- | --- |
| Ethanol | 75 to 99.9 | 80 to 99.5 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Diethyl Acetal | <1 | 0.0001 to 0.1 | 0.0001 to 0.01 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 3, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

What is claimed is:

1. A method for producing ethanol comprising:
hydrogenating alkanoic acid and/or esters thereof in a reactor in the presence of a catalyst to form a crude ethanol mixture comprising acetaldehyde, ethanol, water, and diethyl acetal; and
separating the crude ethanol mixture in the one or more columns to recover an ethanol product comprises less than 1 wt. % diethyl acetal, wherein at least one column is operated above atmospheric pressure.

2. The method of claim 1, wherein the at least one column is operated at a pressure from 100 kPa to 5,000 kPa.

3. The method of claim 1, wherein ethanol is recovered in the residue of the at least one column operated above atmospheric pressure.

4. The method of claim 1, wherein the ethanol product comprises from 0.0001 to 0.01 wt. % diethyl acetal.

5. The method of claim 1, further comprising decomposing at least 10 to 75% of the diethyl acetal in the at least one column is operated above atmospheric pressure.

6. A method for producing ethanol comprising:
hydrogenating alkanoic acid and/or esters thereof in a reactor in the presence of a catalyst to form a crude ethanol mixture;
separating a portion of the crude ethanol mixture in a first distillation column to yield a first residue comprising alkanoic acid, and a first distillate comprising ethanol, and acetaldehyde; and
separating a portion of the first distillate in a second distillation column operated above atmospheric pressure to yield a second residue comprising ethanol, and a second distillate comprising acetaldehyde,
wherein the second residue comprises less than 1 wt. % diethyl acetal.

7. The method of claim 6, wherein the second distillation column is operated at a pressure from 100 kPa to 5,000 kPa.

8. The method of claim 6, wherein the second distillation column is operated at a pressure higher than the first column.

9. The method of claim 6, wherein the second residue comprises from 0.0001 to 0.01 wt. % diethyl acetal.

10. The method of claim 6, further comprising returning a portion of the first residue to the reactor.

11. The method of claim 6, further comprising returning a portion of the second distillate to the reactor.

12. The method of claim 6, wherein the alkanoic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

13. A method for producing ethanol comprising:
providing a crude ethanol mixture comprising acetic acid, acetaldehyde, ethanol, water, and diethyl acetal;
separating a portion of the crude ethanol mixture in a first distillation column to yield a first residue comprising acetic acid, and a first distillate comprising ethanol, and acetaldehyde; and
separating a portion of the first distillate in a second distillation column operated above atmospheric pressure to yield a second residue comprising ethanol, and a second distillate comprising acetaldehyde,
wherein the second residue comprises less than 1 wt. % diethyl acetal.

14. A method for producing ethanol comprising:
hydrogenating alkanoic acid and/or esters thereof in a reactor in the presence of a catalyst to form a crude ethanol mixture;
separating a portion of the crude ethanol mixture in a first distillation column to yield a first residue comprising alkanoic acid, and a first distillate comprising ethanol, water, ethyl acetate, and acetaldehyde;
separating a portion of the first distillate in a second distillation column operated above atmospheric pressure to yield a second residue comprising ethanol and water, and a second distillate comprising ethyl acetate and acetaldehyde; and
separating a portion of the second residue in a third distillation column operated to yield a third residue comprising water, and a third distillate comprising ethanol,
wherein the third distillate comprises less than 1 wt. % diethyl acetal.

15. The method of claim 14, wherein the second distillation column is operated at a pressure from 100 kPa to 5,000 kPa.

16. The method of claim 14, wherein the second distillation column is operated at a pressure higher than the first column.

17. The method of claim 14, wherein the third distillate comprises from 0.0001 to 0.01 wt. % diethyl acetal.

18. The method of claim 14, further comprising returning a portion of the first residue to the reactor.

19. The method of claim 14, further comprising returning a portion of the second distillate to the reactor.

20. The method of claim 14, further comprising returning a portion of the third residue to the second distillation column.

21. A method for producing ethanol comprising:
providing a crude ethanol mixture comprising acetic acid, acetaldehyde, ethanol, water, and diethyl acetal;
separating a portion of the crude ethanol mixture in a first distillation column to yield a first residue comprising acetic acid, and a first distillate comprising ethanol, water, ethyl acetate, and acetaldehyde;
separating a portion of the first distillate in a second distillation column operated above atmospheric pressure to yield a second residue comprising ethanol and water, and a second distillate comprising ethyl acetate and acetaldehyde; and
separating a portion of the second residue in a third distillation column operated to yield a third residue comprising water, and a third distillate comprising ethanol,
wherein the third distillate comprises less than 1 wt. % diethyl acetal.

* * * * *